United States Patent [19]

Mallamo et al.

[11] Patent Number: 5,239,110
[45] Date of Patent: Aug. 24, 1993

[54] PHENYLCYCLOHEXANOL DERIVATIVES AS AGENTS FOR TREATING CNS DISORDERS

[75] Inventors: John P. Mallamo, Kinderhook; William F. Michne, Poestenkill; Aram Mooradian, Schodack, all of N.Y.

[73] Assignee: Sterling Winthrop, Inc., Rensselaer, N.Y.

[21] Appl. No.: 998,233

[22] Filed: Dec. 30, 1992

[51] Int. Cl.$^5$ .................. C07C 91/00; C07C 87/00
[52] U.S. Cl. .................. 560/250; 568/306; 568/308; 568/329; 568/660
[58] Field of Search .......... 560/250; 568/306, 308, 568/329, 660; 514/646, 647, 659

[56] References Cited

U.S. PATENT DOCUMENTS

| | | | |
|---|---|---|---|
| 3,962,259 | 5/1976 | Bauer et al. | 514/646 X |
| 4,028,415 | 6/1977 | Clark | 568/660 X |
| 4,263,317 | 4/1981 | Martin et al. | 424/278 |
| 4,313,959 | 2/1982 | Martin et al. | 424/330 |
| 4,921,524 | 5/1990 | Gilkerson et al. | 560/250 X |
| 4,952,722 | 8/1990 | Serban et al. | 560/250 |

OTHER PUBLICATIONS

Levy, J. and J. Sfiras. "Action of ammonia and dimethylamine on some ethylene oxides of alkylbenzene and phenylchclohexene and their homologs" Compt. rend. 191, 261-3 (1930) [Abstract only].

Primary Examiner—Arthur C. Prescott
Attorney, Agent, or Firm—Paul E. Dupont

[57] ABSTRACT

Compounds of the formula

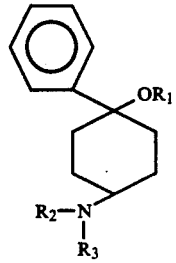

Formula I wherein
  $R_1$ is lower-alkanoyl or hydrogen;
  $R_2$ and $R_3$ are the same or different lower-alkyl; or pharmaceutically acceptable acid-addition salts thereof are useful in the treatment of disorders of the central nervous system.

12 Claims, No Drawings

PHENYLCYCLOHEXANOL DERIVATIVES AS AGENTS FOR TREATING CNS DISORDERS

BACKGROUND OF THE INVENTION a) Field of the Invention

The present invention relates to novel phenyl cyclohexanol derivatives and their pharmaceutically acceptable acid addition salts, pharmaceutical compositions and methods of use thereof as central nervous system disorder treatments.

A number of known antipsychotic drugs are disclosed in the art which have been shown to share a selective, high affinity for sigma receptors, which are sites where psychotomimetic opiates such as (+)-pentazocine and N-allylnormetazocine act. It has been suggested that the antipsychotic behavioral profile of these antipsychotic drugs can be attributed to their role as competitive antagonists of sigma receptor binding and that a systematic screen for drugs that block sigma receptors may provide a valuable strategy for identifying novel antipsychotic agents. Additionally, it has been shown that the relative potencies of these agents studied in vivo correspond well with their relative binding affinities obtained in vitro. See, for example, Snyder and Largent, J. Neuropsychiatry 1989, 1(1), 7-15; Largent et al., Clinical Neuropharmacology 1988, 11(2), 105-119; Taylor et al., Drug Development Research 1987, 11, 65-70; Ferris et al., Life Sciences 1986. 38(25), 2329-2337; and Su et al., Neuroscience Letters 1986, 71, 224-228.

The common property of neuroleptic drugs as sigma receptor ligands suggests that sigma interactions mediate some of the antipsychotic effects of neuroleptics. The distribution of sigma receptors in the limbic areas known to be involved in cognition and emotion supports this view.

b) Information Disclosure Statement

Levy et al. Comp. Rend. 191 p. 261 (1930) describes 2-dimethylamino-1-phenylcyclohexane. No utility for the compounds is disclosed.

Martin et al. U.S. Pat. No. 4,263,317, dated Apr. 21, 1981, discloses spiro[cyclohexane-1,1'(3'H)-isobenzofurans, which reportedly exhibit antidepressant, tranquilizer, analgesic and anticonvulsant activity. The patent also discloses as intermediates compounds of the formula

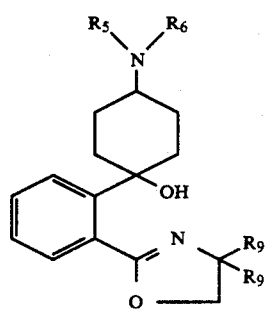

wherein $R_5$, $R_6$ and $R_9$ are lower-alkyl; and the geometric isomers and optical antipodes thereof; and compounds of the formula

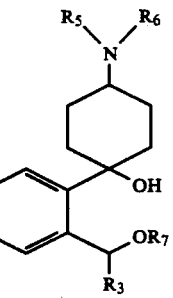

wherein $R_3$ is lower-alkyl or

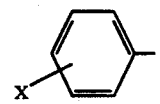

wherein X is hydrogen, halogen or lower-alkyl; $R_5$, $R_6$ and $R_7$ are lower-alkyl; and the geometrical isomers and optical antipodes thereof Martin et al. U.S. Pat. No. 4,313,959, dated Feb. 2, 1982 discloses (arylmethylphenyl-aminocyclohexanols, (arylmethyl)phenyl-aminocyclohexenes and (arylmethyl)phenyl-aminocyclohexanes of the general formula

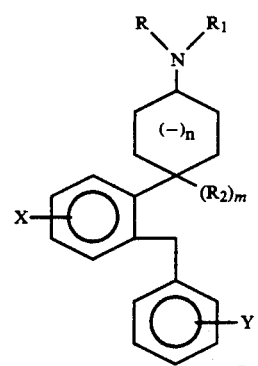

wherein
each of R and $R_1$ is hydrogen or lower-alkyl;
$R_2$ is hydrogen or hydroxyl;
n is an integer or 0 or 1
m is an integer of 0 or 1 and when m is 0 and n is 1, the compound is a cyclohexene derivative;
when m is 1, n is 0 and the compound is a cyclohexane derivative; and
each of X and Y is hydrogen, halogen, alkoxy or 1 or 2 carbon atoms, lower-alkyl, hydroxy and trifluoromethyl. These compounds are said to be useful as antidepressants and anticonvulsants.

SUMMARY OF THE INVENTION

In one aspect the invention provides a compound of the formula

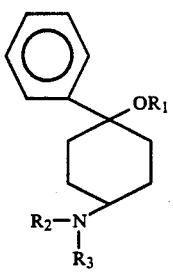

Formula I wherein
- $R_1$ is lower-alkanoyl or hydrogen;
- $R_2$ and $R_3$ are the same or different lower-alkyl; or pharmaceutically acceptable salts thereof.

The compounds of formula I are useful as treatment for disorders of the central nervous system. Accordingly in another aspect the invention provides a pharmaceutical composition containing an effective amount of a compound of formula I in admixture with a suitable carrier In another aspect, the invention relates to methods of treatment of central nervous system disorders.

DETAILED DESCRIPTION INCLUSIVE OF PREFERRED EMBODIMENTS

As used herein, lower-alkyl refers to a straight or branched hydrocarbon radical with 1 to about 4 carbon atoms, for example, methyl, ethyl, propyl, isopropyl, butyl, sec-butyl and the like. Lower-alkanoyl refers to a straight or branched alkanoyl with 2 to about 5 carbon atoms, for example acetyl, propionyl, butyryl, isobutyryl, valeryl and the like.

Preferred compounds are those of formula I wherein $R_1$ is lower-alkanoyl and $R_2$ and $R_3$ are each methyl.

Compounds of formula I are prepared by treating 4-($R_2$-$R_3$amino)cyclohexanone with a nucleophilic phenyl derivative, such as phenyl lithium, phenyl magnesium bromide and the like, in an inert solvent at a temperature from ambient temperature to the boiling point of the solvent preferably under inert atmosphere, giving 1-phenyl-4-($R_2R_3$amino)cyclohexanol (formula I $R_1$=H) This compound can be esterified by known methods, for example by reaction with an appropriate acid anhydride or acid chloride in the presence of an organic base such as triethylamine or dimethylaminopyridine, to afford compounds of formula I wherein $R_1$ is lower-alkanoyl. The 4-($R_2R_3$N)cyclohexanones are either commercially available or can be prepared by methods well known in the art.

It will be appreciated that the compounds of the invention, substituted aminocyclohexanols, exhibit cis/trans isomerism. As used herein, cis isomers are referred to as those having the oxygen and nitrogen substituents on the same side of the cyclohexane ring; and trans having the oxygen and nitrogen substituents on the opposite sides of the cyclohexane ring. In some cases there may be an advantage to using one or the other isomer. Single isomers may be synthesized from analagous cis or trans starting materials or the mixtures may be separated by methods well known in the art, such as chromatography or fractional crystallization.

The compounds of the invention are useful both in the free base form and the form of acid-addition salts, and both forms are within the purview of the invention. The acid-addition salts are in some cases a more convenient form for use, and in practice the use of the salt form inherently amounts to the use of the base form. The acids which can be used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anion. In practicing the present invention, it is convenient to form the hydrochloride, fumarate, toluenesulfonate, hydrogen sulfate, methanesulfonate, or maleate salts. However, other appropriate medicinally acceptable salts within the scope of the invention are those derived from other mineral acids and organic acids. The acid-addition salts of the basic compounds are prepared either by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed only for purposes of purification or identification, or when it is used as an intermediate in preparing a medicinally acceptable salt by ion exchange procedures.

The structures of the compounds of the invention were established by the mode of synthesis, by elemental analysis, and by infrared spectroscopy. In certain cases, compounds were also characterized by nuclear magnetic resonance, or mass spectroscopy. The course of the reactions was assessed by thin layer chromatography (TLC) or high-pressure liquid chromatography (HPLC).

The following examples will further illustrate the invention without, however, limiting it thereto.

It will be appreciated that it is preferred in the art to run reactions in dried solvents and under an inert atmosphere.

EXAMPLE 1

4-(Dimethylamino)-1-phenylcyclohexanol a) To 22.2 g (0.015 mols) 4-dimethylaminocyclohexanone in 300 mL ether was added 90 mL of 1.86 molar phenyllithium in ether/benzene with vigorous stirring. After one-half hour the reaction was quenched with water and the mixture extracted with ether. The ether solution was dried over magnesium sulfate and concentrated in vacuo, giving a white powder. This powder was extracted with cold ether and any crystals remaining were filtered off. A mixture of both the cis and the trans alcohol, 1-phenyl-4-(dimethylamino)

cyclohexanol was obtained. The cis and trans alcohols were then separated as follows:

b) The crystals filtered off in Example 1a (above) had a melting point of 143–146° C. and were but one product by TLC. These were extracted twice with 50 mL warm ether yielding 4.7 g of a white crystalline solid, m.p. 146–149° C. which was determined by NMR to be the trans alcohol.

c) The filtrate from 1b was cooled and a white solid precipitated. Crystals were filtered off and washed in ether. 1 g of a white crystalline solid was obtained. Recrystallization from hexane gave a pure solid with a m.p. of 133-137° C. This sample was determined by NMR to be the cis alcohol.

EXAMPLE 2

Preparation of cis-4-(dimethylamino)-1 phenylcyclohexylacetate (Formula I: $R_2=R_3=CH_3$, $R_1=COCH_3$)

4.7 g of the cis alcohol prepared as described in Example 1c, 4.3 mL of acetic anhydride, 4.3 mL of triethylamine, 0.15 g of 4-dimethylaminopyridine was taken up in 3 mL ether and was stirred overnight. The reaction mixture was treated with water and then basified using sodium carbonate and extracted with ethyl acetate. The ethyl acetate extracts were thoroughly washed with water and evaporated to give 4.6 g of an oil which was treated with 2 mL of diethyl ether and 2 mL of triethylamine and 0.1 g of dimethylaminopyridine. After stirring overnight and working up as above, 4.5 g of an oil was obtained. The mixture was taken up in hexane and passed through a fluorosil column. The eluent was then dried and concentrated in vacuo giving crystals. Finally the crystals were taken up in ether and treated with alcoholic HCl. The resulting solid was filtered off and dried at 75° C. in vacuo overnight yielding 2.6 g of the product as the hydrochloride salt, m.p. 202-204° C.

EXAMPLE 3

Preparation of cis-4-(dimethylamino)-1-phenylcyclohexyl propionate (Formula I: $R_2=R_3=CH_3$, $R_1=COCH_2CH_3$)

6.4 g of the cis alcohol prepared as described in Example 1c was combined with 8.7 mL of propionic anhydride, 14 mL of triethyamine, and 13.5 g of 4-dimethylaminopyridine and stirred at room temperature overnight. Water was added and the product was extracted. This product was absorbed on a fluorosil column and the column was eluted with hexane, then ether, then a 5:1 ether:methanol mixture. The desired product was found in the ether elution and in the beginning of the ether methanol elution. The cis isomer eluted from the column was converted with ethereal HCl to the hydrochloride salt, m.p. 175-183° C.

EXAMPLE 4

Preparation of trans-4(dimethylamino)-1-phenylcyclohexyl propionate (Formula I: $R_1=CH_3CH_2CO$, $R_2=R_3=$methyl)

4.7 g of the trans alcohol of Example 1b was combined with 6 g of propionic anhydride, 5 mL of triethylamine, 0.25 g of dimethylaminopyridine in 5 mL of ether and was stirred overnight over 72 hours. On treatment with water and washing with dilute sodium carbonate and extraction with ether, an oil was obtained which was dissolved in ether and was treated with alcoholic HCL. The precipitate thereby formed was treated with ether and dried yielding 6.1 g of the desired product as the hydrochloride salt, m.p. of 170-172° C.

BIOLOGICAL TEST RESULTS

In standard biological test procedures, representative examples of the compounds of the invention have been found to bind with high affinity to sigma receptors, and are thus useful in the treatment of central nervous system disorders such as psychoses, dystonias, dyskinesias, Parkinson's syndrome, Huntington's chorea, Tourette syndrome, and the like, especially psychoses, e.g., scizophrenic psychoses, manic depressive psychoses and the like.

The sigma receptor binding activity of representative compounds of the inventions was demonstrated by a procedure essentially described by Hudkins and DeHaven-Hudkins, Life Science 1991, 49(17), 1229-1235.

Brain tissue was prepared from male Hartley guinea pigs (Hazelton Labs, Denver, PA) which were anesthetized with CO2 and sacrificed by decapitation. All animal care and use procedures were in accord with the "Guide for the Care and Use of Laboratory Animals" (NIH Publ. No. 86-23, 20 1985). Homogenization was performed in 10 volumes (wt/vol) of 0.32 M sucrose with a Brinkmann Polytron at setting 5, 30 sec. The homogenate was centrifuged at 900×g for 10 min at 4° C., and the supernatant was collected and centrifuged at 22,000×g for 20 min at 4° C. The pellet was resuspended in 10 volumes of Tris-HCl buffer (50 mM, pH 7.4), incubated at 37° C. for 30 min and centrifuged at 22,000×g for 20 min at 4° C. Following this, the pellet was resuspended in Tris buffer and frozen in 5-10 mL aliquots corresponding to a tissue concentration of 100 mg/mL at −70° C. Binding characteristics of the membranes were stable for at least one month when stored at −70° C.

On the day of the assay, membrane aliquots were thawed, resuspended in fresh Tris buffer and stored on ice until use. Each assay tube contained 100 μL of [3H](+)pentazocine at a final concentration of approximately 0.5 nM, [3H]di(2-tolyl)guanidine (DTG) at a final concentration of approximately 4 nM, 100 μL of various concentrations of the compounds of interest, 500 μL of the tissue suspension and 300 μL of buffer to a final assay volume of 1 mL and a final tissue concentration of approximately 8 mg/tube, corresponding to approximately 0.15 mg protein/tube. Nonspecific binding was defined by addition of a final concentration of 1 μM haloperidol to blank tubes for [$^3$H]+pentazocine assay or by addition of a final concentration of 10 μM haloperidol to blank tubes for [$^3$H]DTG assay. All tubes were incubated at 37° C. for 150 minutes ([$^3$H]+pentazocine) or at 25° C. for 90 min ([3H]DTG) before termination of the reaction by filtration over Whatman GF/B glass fiber filters that were presoaked in a solution of 0.5% polyethyleneimine for at least 1 hr prior to use. Filters were washed with three 4 mL volumes of cold Tris-HCl buffer.

Following addition of scintillation cocktail, samples were allowed to equilibrate for at least 4 hr. The amount of bound radioactivity was determined by liquid scintillation spectrometry using a Beckman LS 5000 TA liquid scintillation counter with an efficiency for tritium of approximately 60%.

The following Table summarizes the results obtained from the testing of representative compounds of the invention.

Data obtained on the compounds in the di(2-tolyl)-guanidine (DTG) and d-pentazocine (+pent) assays, expressed as a Ki value in nM or % inhibition at 10 nM, are as follows:

| Example | DTG Ki (nM) | % inhib (10 nM) | + Pent Ki (nM) |
|---------|-------------|-----------------|----------------|
| 1 | — | 61% | — |
| 2 | 5003 | — | — |
| 3 | 288 | — | 78 |
| 4 | 4076 | — | — |

The compounds of the invention can be prepared for pharmaceutical use by conventional pharmaceutical procedures that are well known in the art; that is by formulating a pharmaceutical composition which comprises compounds of the invention or their pharmaceutically acceptable salts together with one or more physiologically acceptable carriers, adjuvants, diluents or vehicles, for oral administration in solid or liquid form, parenteral administration, topical administration or aerosol inhalation administration, and the like.

Solid compositions for oral administration include compressed tablets, pills, powders and granules. In such solid compositions, the active compound is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutcially acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting emulsifying and dispersing agents.

Preparations according to the invention for topical administration or aerosol inhalation administration include dissolving or suspending a compound of the invention in a pharmaceutically acceptable vehicle such as water, aqueous alcohol, glycol, oil solution or oil-water emulsion and the like.

If desired, the compounds of the invention can further be incorporated into slow release or targeted delivery systems such as polymer matrices, liposomes, and microspheres.

The percentage of active component in such compositions may be varied so that a suitable dosage is obtained. The dosage administered to a particular patient is variable depending upon the clinician's judgment using as criteria: The route of administration, the duration of treatment, the size and physical condition of the patient, the potency of the active component and the patient's response thereto. An effective dosage amount of the active component can thus readily be determined by the clinician after a consideration of all criteria and using his best judgment on the patient's behalf.

I claim:

1. A compound of the formula

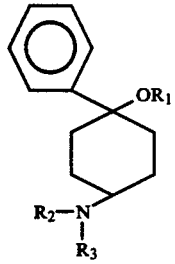

Formula I wherein
$R_1$ is lower-alkanoyl or hydrogen;
$R_2$ and $R_3$ are the same or different lower-alkyl; or pharmaceutically acceptable acid addition salts thereof.

2. A compound according to claim 1 wherein $R_1$ is loweralkanoyl, $R_2$ and $R_3$ are methyl.

3. A compound according to claim 2 selected from: Cis-4-(dimethylamino)-1-phenylcyclohexyl acetate, Trans-4-(dimethylamino)-1-phenylcyclohexyl acetate, Cis-4-(dimethylamino)-1-phenylcyclohexyl propionate, and 4-(dimethylamino)-1-phenylcyclohexanol.

4. A pharmaceutical composition comprising a pharmaceutical carrier and as an active ingredient a compound according to claim 1.

5. A pharmaceutical composition comprising a pharmaceutical carrier and as an active ingredient a compound according to claim 2.

6. A pharmaceutical composition comprising a pharmaceutical carrier and as an active ingredient a compound according to claim 3.

7. A method for treatment of central nervous system disorders, comprising administering to a patient in need of such treatment a medicament containing an effective amount of a compound according to claim 1.

8. A method for treatment of central nervous system disorders, comprising administering to a patient in need of such treatment a medicament containing an effective amount of a compound according to claim 2.

9. A method for treatment of central nervous system disorders, comprising administering to a patient in need of such treatment a medicament containing an effective amount of a compound according to claim 3.

10. A method for treatment of central nervous system disorders, comprising administering to a patient in need of such treatment a composition according to claim 4.

11. A method for treatment of central nervous system disorders, comprising administering to a patient in need of such treatment a composition according to claim 5.

12. A method for treatment of central nervous system disorders, comprising administering to a patient in need of such treatment a composition according to claim 6.

* * * * *